(12) United States Patent
Kitchens

(10) Patent No.: US 6,916,323 B2
(45) Date of Patent: Jul. 12, 2005

(54) METHOD AND APPARATUS FOR PERCUTANEOUSLY SECURING A BONE SCREW AND A BONE PLATE TO A BONE OF A PATIENT

(75) Inventor: David Gregory Kitchens, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 200 days.

(21) Appl. No.: 09/934,052

(22) Filed: Aug. 21, 2001

(65) Prior Publication Data

US 2003/0040752 A1 Feb. 27, 2003

(51) Int. Cl.⁷ .............................................. A61F 5/00
(52) U.S. Cl. ......................... 606/86; 606/99; 606/104; 606/69
(58) Field of Search .......................... 606/69, 70, 71, 606/53, 86, 96, 99, 103, 104, 65, 66

(56) References Cited

U.S. PATENT DOCUMENTS

| | | |
|---|---|---|
| 4,432,358 A | 2/1984 | Fixel |
| 4,438,762 A | 3/1984 | Kyle |
| 4,450,834 A * | 5/1984 | Fischer .................... 606/80 |
| 4,465,065 A | 8/1984 | Gotfried |
| 4,545,374 A | 10/1985 | Jacobson |
| 4,612,920 A | 9/1986 | Lower |
| 4,617,922 A | 10/1986 | Griggs |
| 4,621,629 A | 11/1986 | Koeneman |
| 4,640,271 A | 2/1987 | Lower |
| 4,657,001 A | 4/1987 | Fixel |
| 4,672,957 A * | 6/1987 | Hourahane ............... 606/80 |
| 4,827,917 A | 5/1989 | Brumfield |
| 4,860,735 A * | 8/1989 | Davey et al. ............ 606/80 |
| RE33,348 E | 9/1990 | Lower |
| 4,973,333 A | 11/1990 | Treharne |
| 5,032,125 A | 7/1991 | Durham et al. |
| 5,041,116 A | 8/1991 | Wilson |
| 5,087,260 A | 2/1992 | Fixel |
| 5,122,133 A | 6/1992 | Evans |
| 5,167,663 A | 12/1992 | Brumfield |
| 5,190,528 A | 3/1993 | Fonger et al. |

(Continued)

FOREIGN PATENT DOCUMENTS

| | | |
|---|---|---|
| EP | 0 617 927 A1 | 10/1994 |
| WO | WO 98/01078 | 1/1998 |
| WO | WO 99/42053 | 8/1999 |

OTHER PUBLICATIONS

PCT Search Report for PCT/US02/26470, Aug. 20, 2002, 9 pages.

(Continued)

*Primary Examiner*—Eduardo C. Robert
(74) *Attorney, Agent, or Firm*—Barnes & Thornburg

(57) ABSTRACT

A method of percutaneously implanting a first component and a second component of an orthopaedic assembly into a body of a patient includes the steps of securing a first instrument to the first component, and advancing the first component into the body of the patient. The first instrument is advanced into the body of the patient such that a portion of the first instrument extends out of the body. A second instrument is secured to the second component, and the second component is advanced into the body of the patient. The second instrument is advanced into the body of the patient such that a portion of the second instrument extends out of the body. A third instrument is advanced into contact with both the first instrument and the second instrument so as to position the first component and the second component in a predetermined position relative to one another. An instrument assembly for percutaneously implanting an orthopaedic assembly is also disclosed.

7 Claims, 16 Drawing Sheets

U.S. PATENT DOCUMENTS

| | | |
|---|---|---|
| 5,201,733 A | 4/1993 | Etheredge, III |
| 5,312,406 A | 5/1994 | Brumfield |
| 5,324,292 A | 6/1994 | Meyers |
| 5,376,125 A | 12/1994 | Winkler |
| 5,429,641 A | 7/1995 | Gotfried |
| 5,534,005 A * | 7/1996 | Tokish et al. .................. 606/80 |
| 5,562,666 A | 10/1996 | Brumfield |
| 5,649,930 A * | 7/1997 | Kertzner ...................... 606/96 |
| 5,658,339 A | 8/1997 | Tronzo et al. |
| 5,806,117 A | 9/1998 | Gotfried |
| 5,810,821 A | 9/1998 | Vandewalle |
| 5,928,239 A | 7/1999 | Mirza |
| 5,976,145 A * | 11/1999 | Kennefick, III .............. 606/80 |
| 6,022,352 A | 2/2000 | Vandewalle |
| 6,127,597 A | 10/2000 | Beyar et al. |

OTHER PUBLICATIONS

Lee Beadling, "Trauma–Minimally invasive hip fracture treatment has advantages for elderly", Orthopedics Today, Mar. 2001, 3 pages.

DePuy ACE Medical Company, "ACE Titanium Surgical Technique", 1996, 24 pages.

DePuy ACE Medical Company, "TK2™ Compression Hip Screw System—Application and Technique Information", 2000, 12 pages.

* cited by examiner

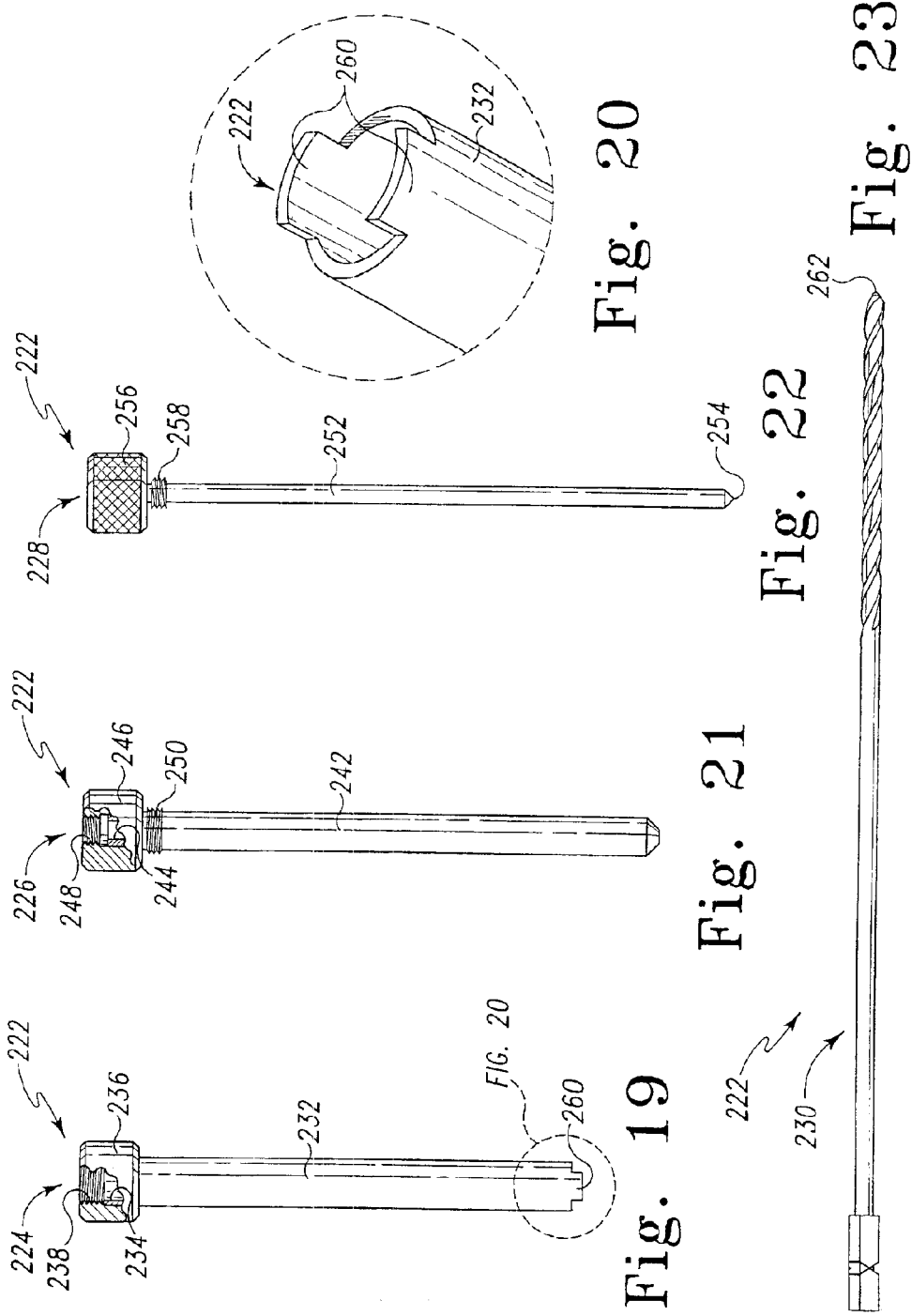

METHOD AND APPARATUS FOR PERCUTANEOUSLY SECURING A BONE SCREW AND A BONE PLATE TO A BONE OF A PATIENT

FIELD OF THE INVENTION

The present invention relates generally to implantable bone screws and bone plates, and more particularly to a method and apparatus for percutaneously securing a bone screw and a bone plate to a bone of a patient.

BACKGROUND OF THE INVENTION

Minimally invasive surgical techniques have been developed for many different types of surgical procedures. Such techniques attempt to balance the need to achieve the goal of the surgical procedure while minimizing the surgical injury to the patient. As such, surgeries performed by use of minimally invasive techniques generally result in lower postoperative morbidity, shorter postoperative hospital stay, less postoperative pain, decreased cost, and quicker recovery as compared to "open" or conventional surgical techniques. Because of the aforementioned advantages, these minimally invasive techniques are being applied to an increasing variety of surgical procedures. For example, minimally invasive techniques in the form of laparoscopic procedures, such as a laparoscopic colectomy for carcinoma of the colon, have been developed.

However, despite growing use in other surgical fields, minimally invasive techniques have not been significantly developed for use in orthopaedic procedures. In particular, although orthopaedic surgeons have recognized the general principle that maintenance of soft tissue contributes significantly to the post operative healing process, conventional techniques in which the soft tissue is completely opened to gain complete access to the bone structure thereunder are still in wide spread use. One reason for this is the unique nature of many orthopaedic procedures. In particular, orthopaedic procedures often involve the "delivery" (i.e., implantation) of devices which are relatively large in design compared to the "deliverables" associated with other forms of surgery. Specifically, in the case of, for example, an appendectomy, minimally invasive techniques are readily adaptable since the surgeon may aptly remove the subject tissue (i.e., the patient's appendix) and thereafter deliver and install the necessary sutures through the relatively small confines of a cannula of a trocar. However, in the case of, for example, trauma repair of a heavily fractured long bone (e.g., a femur or tibia), a number of relatively large plates are screwed or otherwise fastened to the fracture bone. The size of such plates has long since been viewed as prohibiting in regard to the use of minimally invasive techniques for the implantation of such components.

As such, orthopaedic surgeons have typically preferred to open the soft tissue surrounding the bone to be treated in order to completely expose the surgical site thereby providing for ease of plate delivery. As a result of such continued use of "open" procedures, soft tissue surrounding the bone continues to be compromised thereby impairing normal blood circulation to the treated bone, potentially delaying fracture healing, and potentially increasing the risk of infection. Indeed, although the majority of patients treated with such procedures heal without complication, there are certain occasions in which complications such as infection or refracture occur thereby prolonging healing rates and, in certain cases, increasing the rates of secondary revisions.

As a result of the aforedescribed shortcomings associated with traditional orthopaedic surgeries, along with the promise associated with minimally invasive techniques, a number of attempts have been made to provide certain of the advantages associated with minimally invasive techniques to certain orthopaedic procedures. For example, plate fixation assemblies have heretofore been developed for use in fracture repair of femurs. However, such assemblies suffer from a number of drawbacks. For example, such assemblies suffer from a certain degree of inflexibility in regard to the manner in which the orthopaedic component is implanted. For instance, the prosthesis utilized with such assemblies must generally be "pre-assembled" prior to implantation thereof. Specifically, since it is difficult, if not impossible, for the surgeon to visualize the implanted prosthesis, in vivo assembly of the prosthesis is rendered equally difficult, if not impossible.

What is needed therefore is an apparatus and method for use in the performance of minimally invasive orthopaedic procedures which overcome one or more of the above-mentioned drawbacks.

SUMMARY OF THE DISCLOSURE

The present invention provides for percutaneous implantation of orthopaedic assemblies thereby eliminating the need to utilize relatively elongated incisions. The concepts of the present invention are particularly useful in regard to the implantation and installation of bone plates to the long bones of the human skeletal system such as the femur. In practice, the concepts of the present invention allow for implantation of a hip screw and bone plate through a relatively small incision (e.g., 2–3 centimeters). Once implanted, the hip screw and bone plate may be aligned and engaged with one another by use of the apparatus and techniques described herein. By utilizing such a small incision relative to heretofore utilized techniques (e.g., "open" incisions), the concepts of the present invention reduce the number of occurrences of postoperative complications such as infection, refracture, or prolonged healing rates.

In accordance with one illustrative embodiment of the present invention, there is provided a method of percutaneously implanting a first component and a second component of an orthopaedic assembly into a body of a patient. The method includes the steps of securing a first instrument to the first component, and advancing the first component into the body of the patient. The first instrument is advanced into the body of the patient such that a portion of the first instrument extends out of the body. A second instrument is secured to the second component, and the second component is advanced into the body of the patient. The second instrument is advanced into the body of the patient such that a portion of the second instrument extends out of the body. A third instrument is advanced into contact with both the first instrument and the second instrument so as to position the first component and the second component in a predetermined position relative to one another.

In accordance with another illustrative embodiment of the present invention, there is provided an instrument assembly for percutaneously implanting an orthopaedic assembly. The instrument assembly includes a first instrument which is adapted to be secured to a first orthopaedic component. The first instrument has a first alignment feature. The instrument assembly also includes a second instrument which is adapted to be secured to a second orthopaedic component. The second instrument has a second alignment feature. The instrument assembly further includes a third instrument having a third alignment feature which is adapted to cooperate with the first alignment feature and the second alignment feature so as to position the first instrument and the second instrument in a predetermined position relative to one another.

In accordance with another illustrative embodiment of the present invention, there is provided a method of percutaneously securing a bone plate to a bone within a body of a patient. The method includes the step of securing a screw locating instrument to a bone screw. The bone screw is screwed into the bone of the patient. The screw locating instrument is advanced into the body of the patient such that a portion of the screw locating instrument extends out of the body. In addition, a plate locating instrument is secured to the bone plate, and the bone plate is advanced into the body of the patient. The plate locating instrument is advanced into the body of the patient such that a portion of the plate locating instrument extends out of the body. An alignment instrument is advanced into contact with both the screw locating instrument and the plate locating instrument so as to position the bone screw and the bone plate in a predetermined position relative to one another.

In a specific exemplary embodiment for use in a hip repair procedure, there is provided an instrument assembly for percutaneously implanting a hip screw and a bone plate. The instrument assembly includes a screw locating instrument which is adapted to be secured to the hip screw. The screw locating instrument has a first alignment feature. The instrument assembly also includes a plate locating instrument which is adapted to be secured to the bone plate. The plate locating instrument has a second alignment feature. An alignment instrument has a third alignment feature which is adapted to cooperate with the first alignment feature and the second alignment feature so as to position the screw locating instrument and the plate locating instrument in a predetermined position relative to one another thereby positioning the hip screw and the bone plate relative to one another.

BRIEF DESCRIPTION OF THE DRAWINGS

FIG. 19 is an elevational view of a screw sleeve;

FIG. 20 is an enlarged fragmentary perspective view of a portion of FIG. 19 which is encircled and indicated as FIG. 20;

FIG. 21 is an elevational view of a drill guide;

FIG. 22 is an elevational view of a trocar; and

FIG. 23 is an elevational view of a bone drill.

DETAILED DESCRIPTION OF AN ILLUSTRATIVE EMBODIMENT

Figure 1:
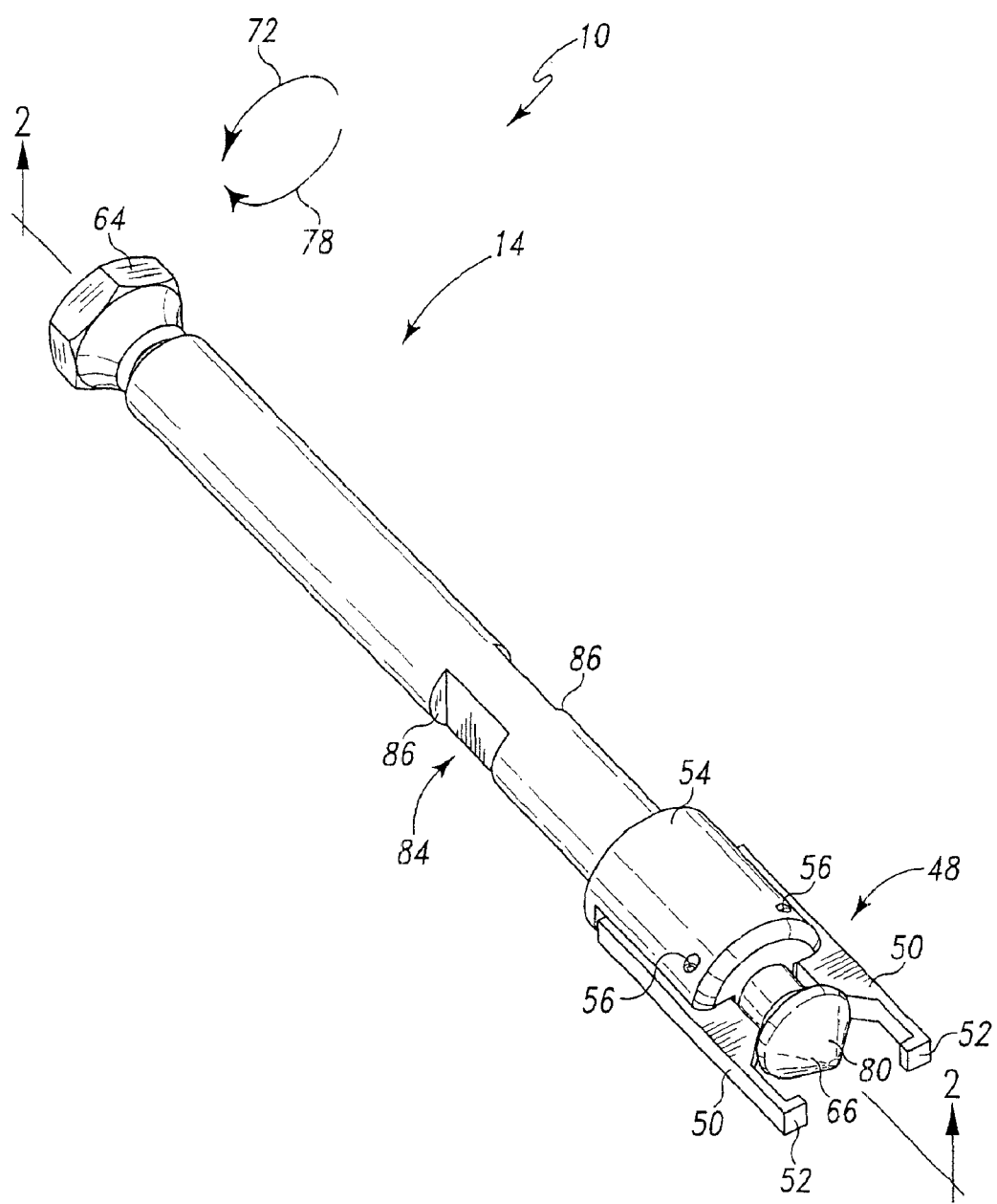
FIG. 1 is a perspective view of a bone screw locating instrument.

While the invention is susceptible to various modifications and alternative forms, specific exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIGS. 1–7, there is shown an instrument assembly 10 which may be utilized to percutaneously implant a surgical device into a body of a patient. As will be discussed below in greater detail, use of the instrument assembly 10, along with the associated techniques, allows for the implantation of such a device through a relatively small incision thereby providing numerous advantages associated with minimally invasive surgical techniques including a reduction in the number of postoperative complications such as infection, refracture, or prolonged healing rates. One particularly useful implementation of the concepts of the present invention relates to the percutaneous implantation of a bone plate 12 (see FIGS. 9–11) during treatment of a fractured long bone such as a femur 200 (see FIGS. 12–18). As such, the concepts of the present invention will herein be described in regard to the percutaneous implantation and securement of the femoral bone plate 12; however, it should be appreciated that such a description is exemplary in nature and that other applications of the concepts of the present invention are contemplated.

Figure 5:
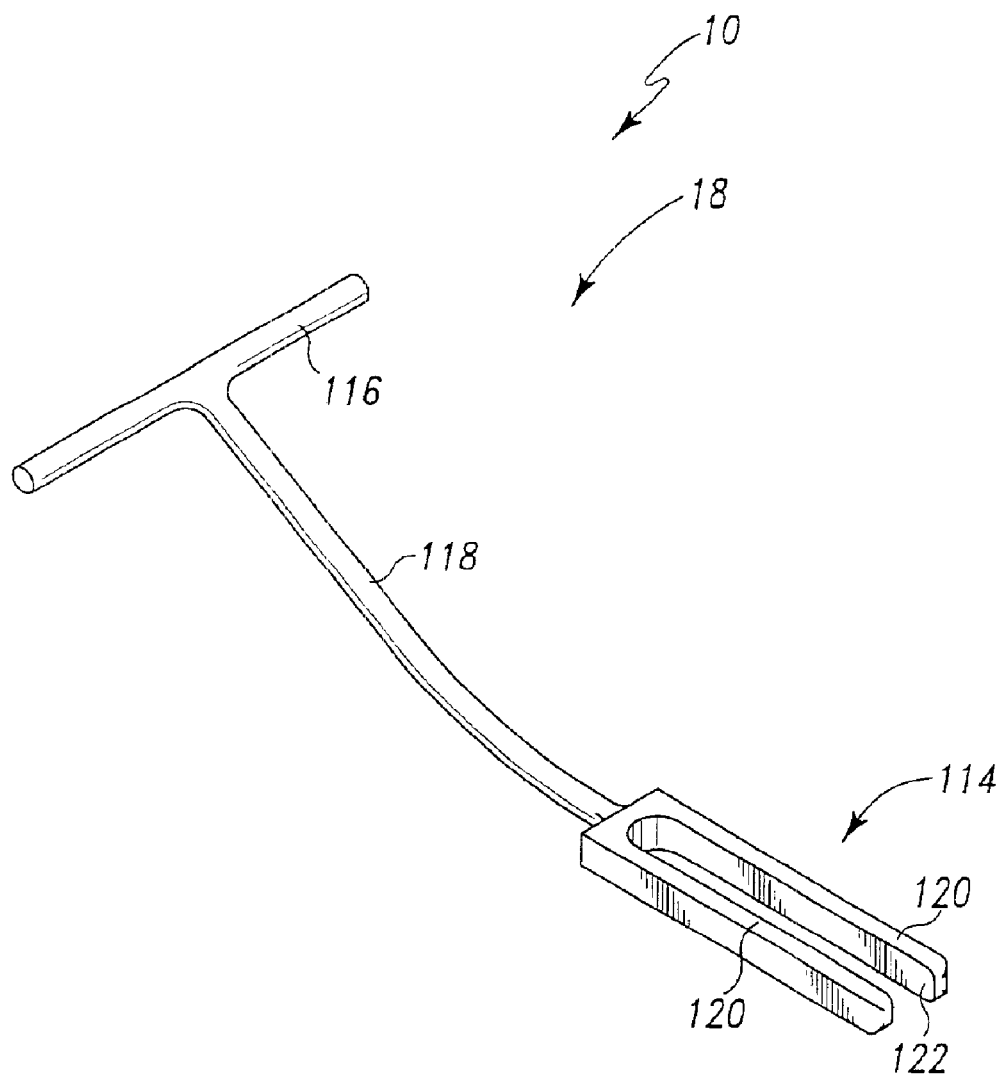
FIG. 5 is a perspective view of an alignment instrument.
Figure 6:
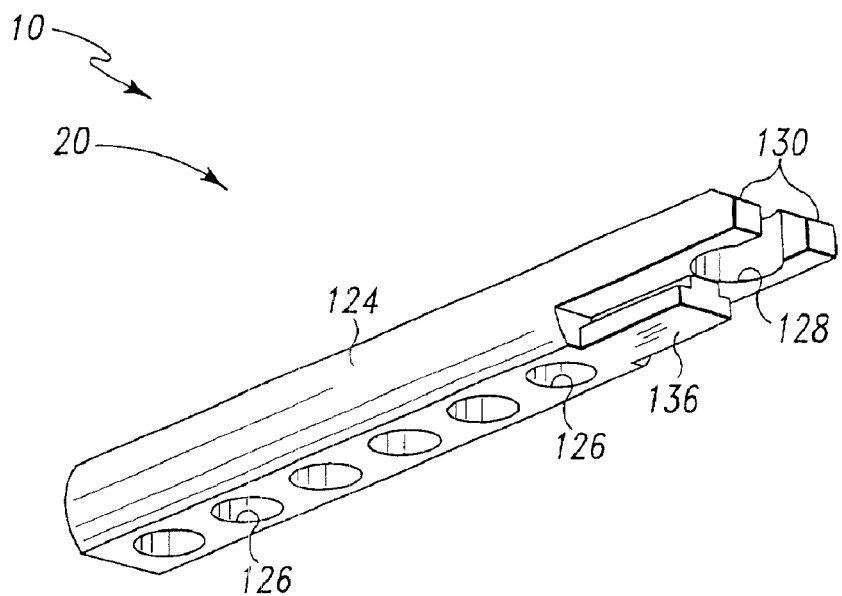
FIGS. 6 and 7 are perspective views of a screw targeting instrument.
Figure 7:
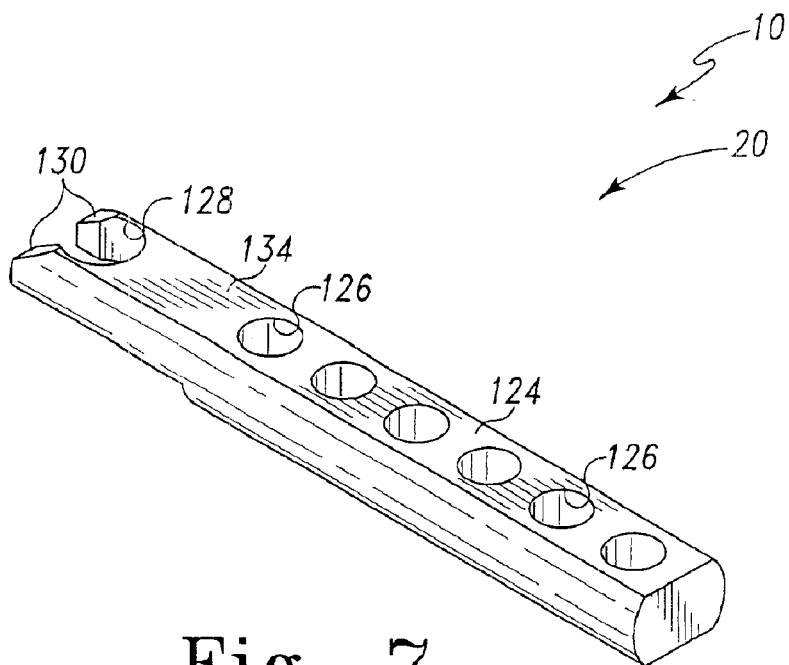

The instrument assembly 10 includes a screw locating instrument 14 (see FIGS. 1 and 2), a plate locating instrument 16 (see FIGS. 3 and 4), an alignment instrument 18 (see FIG. 5), and a screw targeting instrument 20 (see FIGS. 6 and 7). The screw locating instrument 14 is utilized to maintain a bone screw such as a hip lag screw assembly 22 (see FIG. 8) in a desired orientation subsequent to implantation thereof. In one exemplary embodiment, the lag screw assembly 22 includes an outer barrel 24 with a screw 26 captured therein. The screw 26 includes a shaft 28 having a number of threads 30 on one end thereof and a head 32 on its other end.

Figure 8:
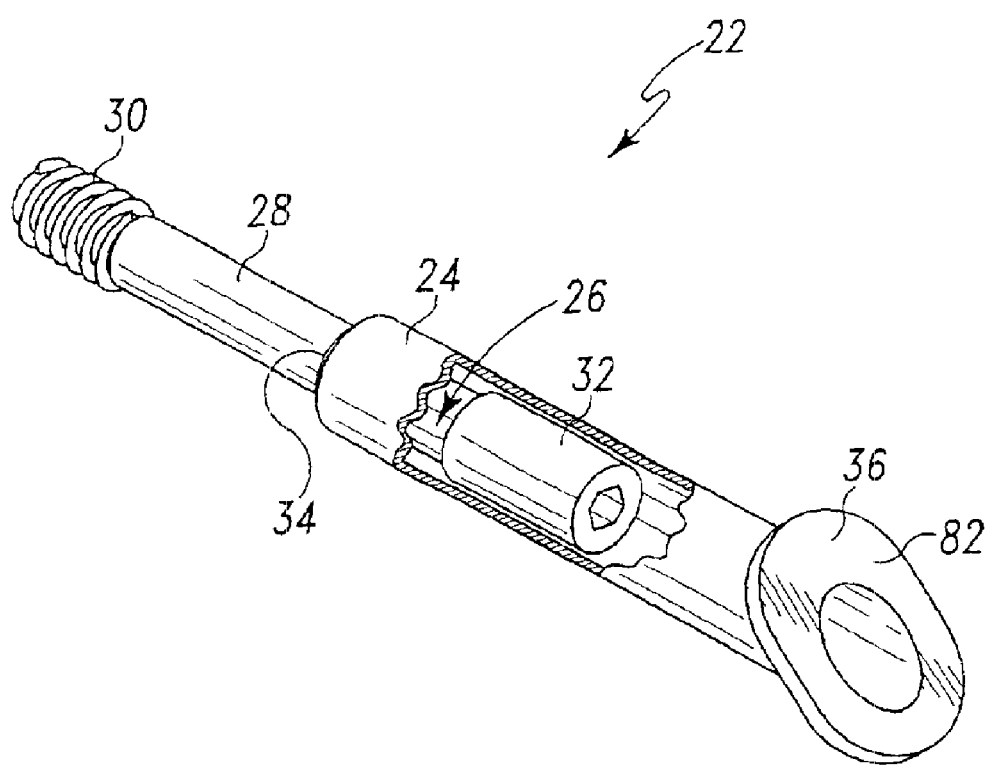
FIG. 8 is a partial cutaway perspective view of a bone lag screw assembly.

The configuration of the threads 30 and the head 32 of the screw 26 prevent the screw 26 from becoming separated from the barrel 24. In particular, as shown in FIG. 8, the shaft 28 of the screw 26 extends out of a hole 34 defined in one end of the barrel 24. The head 32 of the screw 26 has a diameter which is larger than the diameter of the hole 34 thereby preventing the head 32 from being advanced in a first direction through the hole 34 and hence out of the barrel 24. Similarly, the diameter of the threads 30 is likewise greater than the diameter of the hole 34 thereby preventing the screw 26 from being advanced through the hole 34 and hence into (and thereafter out of) the barrel 24 in the opposite direction.

The barrel 24 of the lag screw assembly 22 has a flange 36 secured thereto. As shown in FIG. 8, the flange 36 is secured to the end of the barrel 24 opposite of the hole 34.

The flange 36 is non-rotatably secured to the barrel 24 by way of being integrally formed therewith or by use of securement techniques such as welding. As shall be discussed below in greater detail, the flange 36 cooperates with features defined in the bone plate 12 in order to secure the two components to one another.

Figure 9:
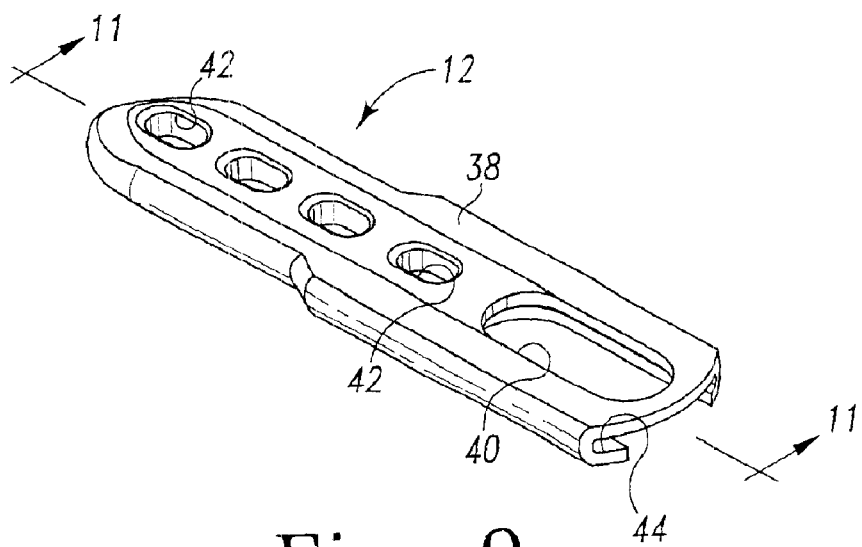
FIG. 9 is a perspective view of a bone plate.
Figure 10:
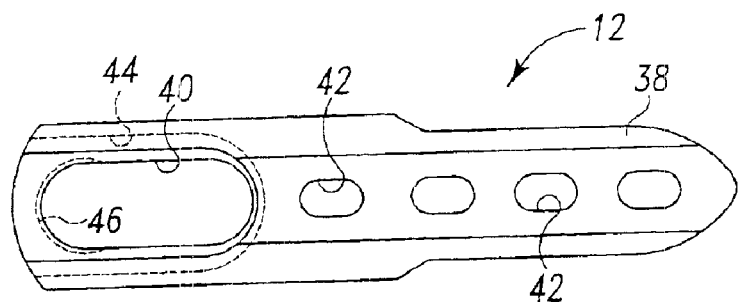
FIG. 10 is a bottom elevational view of the bone plate of FIG. 9.
Figure 11:
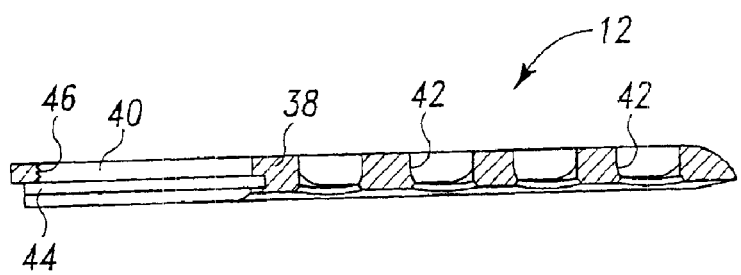
FIG. 11 is a cross sectional view taken along the line 11—11 of FIG. 9, as viewed in the direction of the arrows.

As shown in FIGS. 9–11, the bone plate 12 has an elongated body 38 having a slot 40 and a number of holes 42 defined therein. As will be discussed below in greater detail, the hip lag screw assembly 22 is positionable so as to be accessible through the slot 40, whereas a number of bone screws 212 (see FIG. 18) may be advanced through the holes 42 and thereafter secured to the femur 200. It should be appreciated that although the bone plate 12 is herein described and shown in the drawings as having four holes 42, any number of holes 42 may be defined in the plate 12 in order to allow the plate 12 to conform to a particular femoral anatomy or to allow for repair of any type of femoral fracture.

Figure 17:
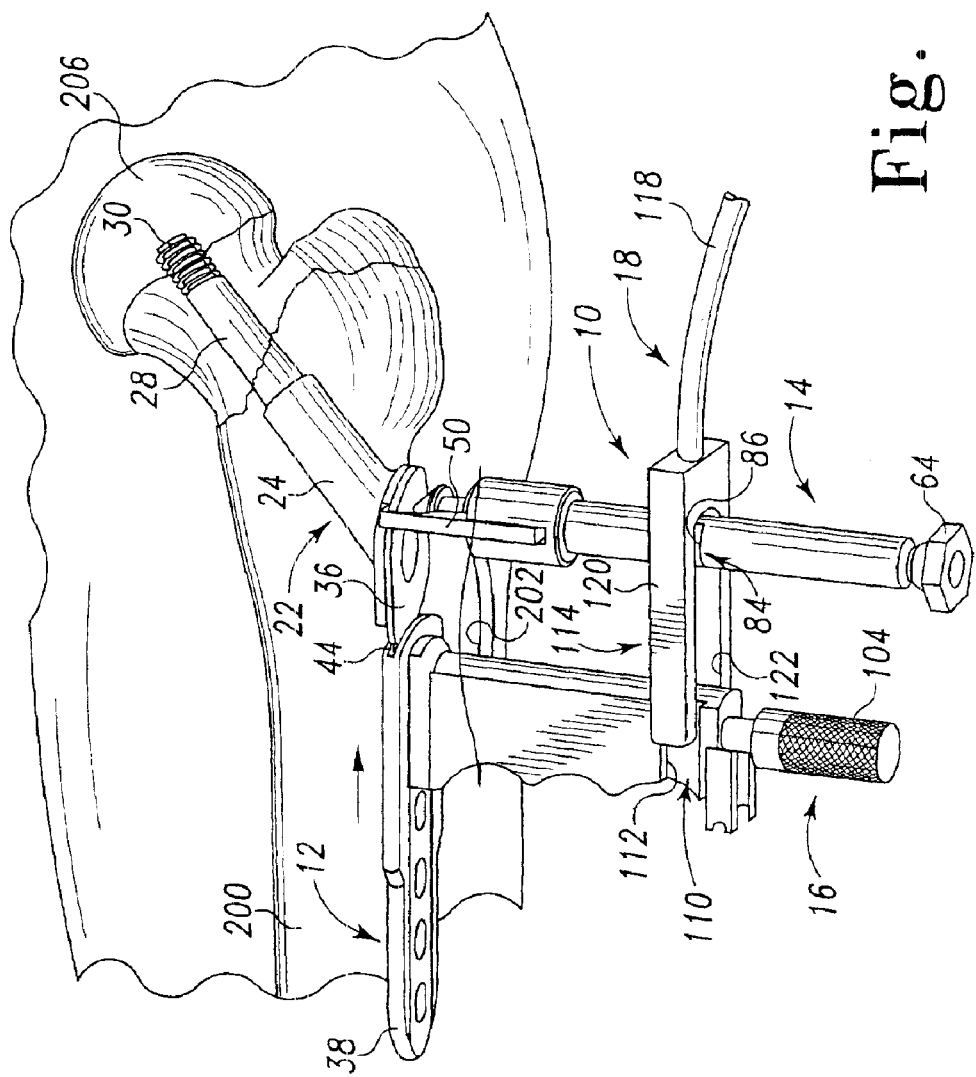
Figure 18:
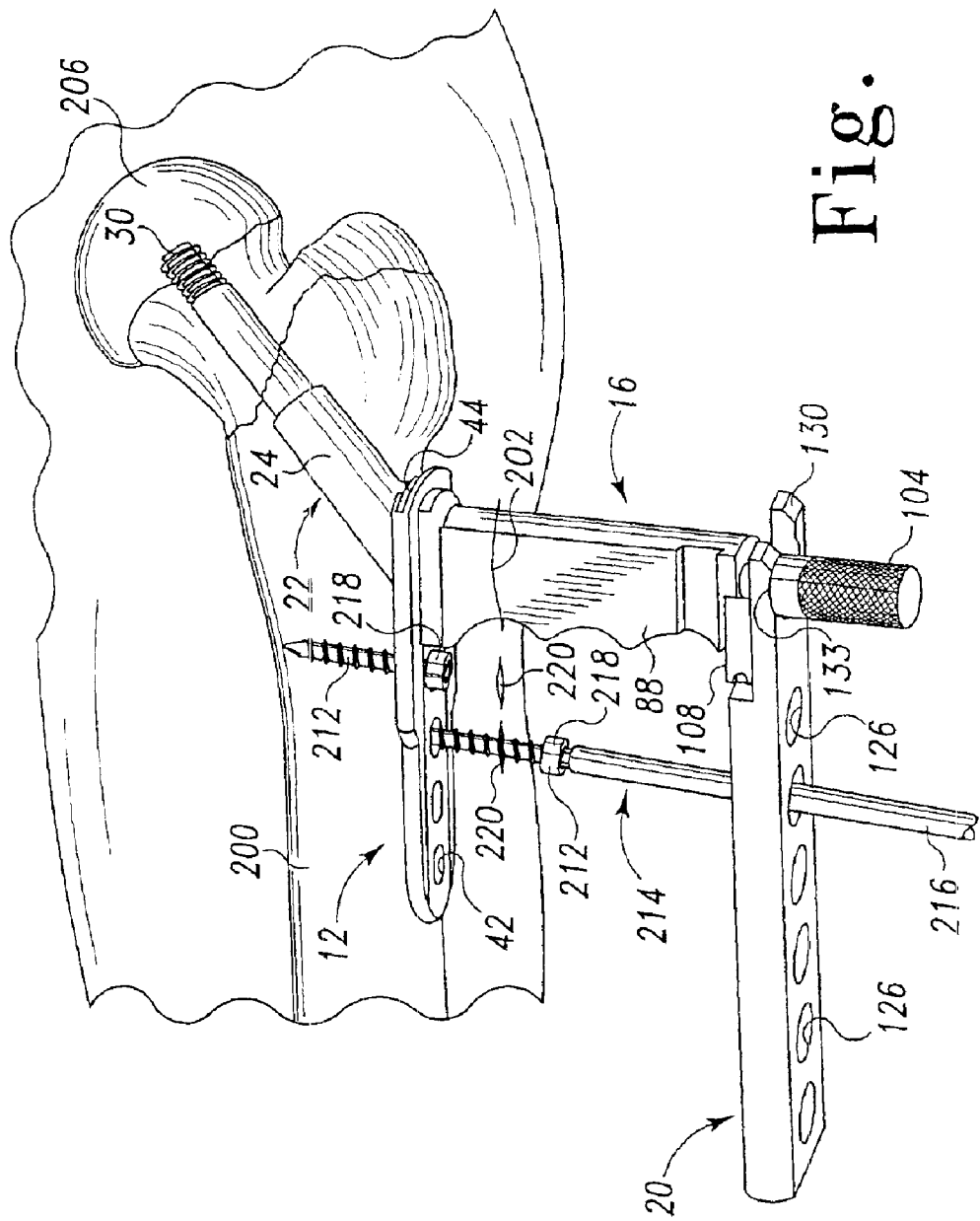

As shown in FIG. 10, a first end of the body 38 of the bone plate 12 has a rounded or bullet-shaped configuration. Such a shape allows for ease of insertion of the plate through the underlying tissues during percutaneous implantation of the plate 12. As shown in FIGS. 9 and 10, the opposite end of the body 38 of the bone plate 12 has a channel 44 defined therein. As shown in FIGS. 17 and 18, the flange 36 of the lag screw assembly 22 may be received into the channel 44 in order to secure the lag screw assembly 22 to the bone plate 12.

As shown in FIGS. 10 and 11, the sidewall of the body 38 at one end of the slot 40 has a number of threads 46 defined therein. In an exemplary embodiment, the threads 46 extend through approximately 180° of the sidewall of the slot 40. As will be discussed below in greater detail, the threads 46 may be engaged by a surgical instrument in order to secure the bone plate 12 to the instrument during implantation of the plate 12.

As described above, the screw locating instrument 14 is provided to maintain the lag screw assembly 22 in a desired position and/or orientation during a percutaneous orthopaedic procedure. In order to do so, the screw locating instrument 14 is adapted to be selectively secured to the lag screw assembly 22. Specifically, the screw locating instrument 14 includes an attachment mechanism 48 having a pair of locking arms 50. The locking arms 50 have a barb 52 on one end thereof which engages the backside of the flange 36 of the lag screw assembly 22. The locking arms 50 are pivotally secured to an outer sleeve 54 of the instrument 14 by use of a pair of pivot pins 56. A pair of springs 58 (see FIG. 2) apply a bias to the end of each of the locking arms 50 opposite to the barbs 52 in order to urge the barbs 52 toward one another. It should be appreciated that when urged toward one another in such a manner, the barbs 52 may be utilized to engage the backside of the flange 36 of the lag screw assembly 22 thereby securing the instrument 14 thereto.

The screw locating assembly 14 has an elongated rod 60 which extends through an elongated bore 62 defined in the outer sleeve 54. The rod 60 has a knob 64 non-rotatably secured to one end thereof, whereas the other end of the rod 60 has a beveled tip 66 defined therein. A portion of the rod 60 located between the beveled tip 66 and the knob 64 has a number of threads 68 defined therein. The threads 68 threadingly engage a number of corresponding threads 70 defined in the sidewall of the bore 62.

Rotation of the knob 64 in the general direction of arrow 72 of FIG. 1 causes similar rotation (i.e., in the direction of arrow 72 of FIG. 1) of the rod 60. Such rotation of the rod 60 causes the threads 68 of the rod 60 to threadingly engage the threads 70 of the sleeve 54 in a manner which extends or otherwise urges the beveled tip 66 outwardly in a direction away from the sleeve 54. Such outward movement of the beveled tip 66 causes a cam surface 74 defined in the tip 66 to be spaced a part from a cam surface 76 defined in each of the locking arms 50 thereby allowing the springs 58 to urge the locking arms 50 inwardly toward one another.

Conversely, rotation of the knob 64 in the opposite direction (i.e, in the general direction of arrow 78 of FIG. 1) causes similar rotation (i.e., in the direction of arrow 78 of FIG. 1) of the rod 60. Such rotation of the rod 60 causes the threads 68 of the rod 60 to threadingly engage the threads 70 of the sleeve 54 in a manner which retracts or otherwise urges the beveled tip 66 inwardly in a direction toward the sleeve 54. Such inward movement of the beveled tip 66 causes the cam surface 74 of the tip 66 to be urged into contact with the cam surfaces 76 of the locking arms 50 thereby overcoming the bias of the springs 58 so as to urge the locking arms 50 outwardly in a direction away from one another. In this manner, the barbs 52 of the locking arms 50 may be disengaged from the flange 36 of the lag screw assembly 22.

It should be appreciated that in addition to the aforedescribed cam feature, the configuration of the beveled tip 66 facilitates the initial engagement of the screw locating instrument 14 to the lag screw assembly 22. In particular, the conically-shaped outer surface 80 of the beveled tip 66 functions as a "spear" for guiding the tip 66 onto an upper surface 82 defined in the flange 36 of the lag screw assembly 22 (see FIG. 8) during securement of the screw locating instrument 14 to the lag screw assembly 22.

Figure 2:
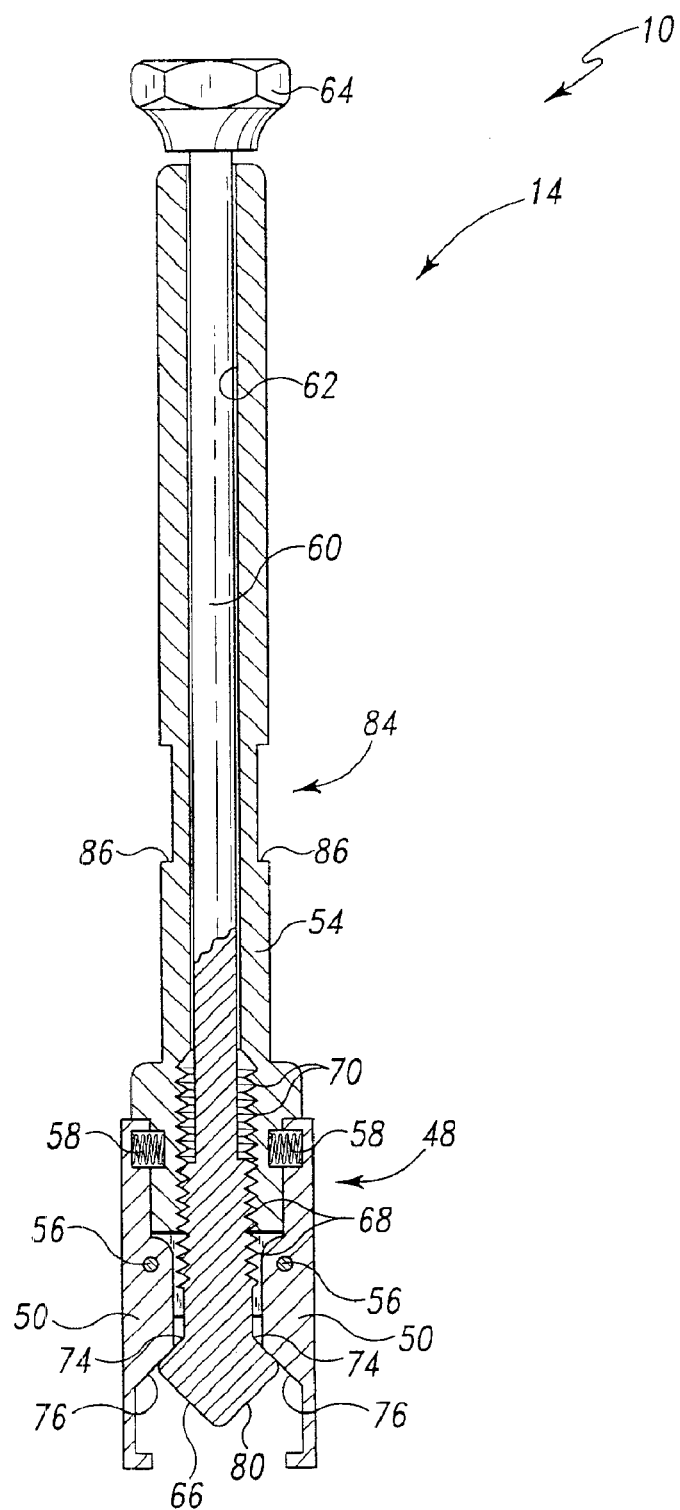
FIG. 2 is a cross sectional view taken along the line 2—2 of FIG. 1, as viewed in the direction of the arrows, note that the knob and a portion of the rod are not shown in cross section for clarity of description.

As shown in FIGS. 1 and 2, the screw locating instrument 14 may be configured to include an alignment feature 84. The alignment feature 84 is provided to cooperate with features or mechanisms associated with other instruments such as the plate locating instrument 16 and the alignment instrument 18 in order to position the screw locating instrument 14 (and hence the lag screw assembly 22) in a desired position and/or orientation.

In one exemplary embodiment, the alignment feature 84 of the screw locating instrument 14 is embodied as a pair of recesses 86. As will be discussed below in greater detail, a portion of the alignment instrument 18 may be advanced into the recesses 86 of the screw locating instrument 14, along with similar recesses defined in the plate locating instrument 16, in order to align or otherwise position the instruments 14, 16 in a predetermined position relative to one another.

Figure 3:
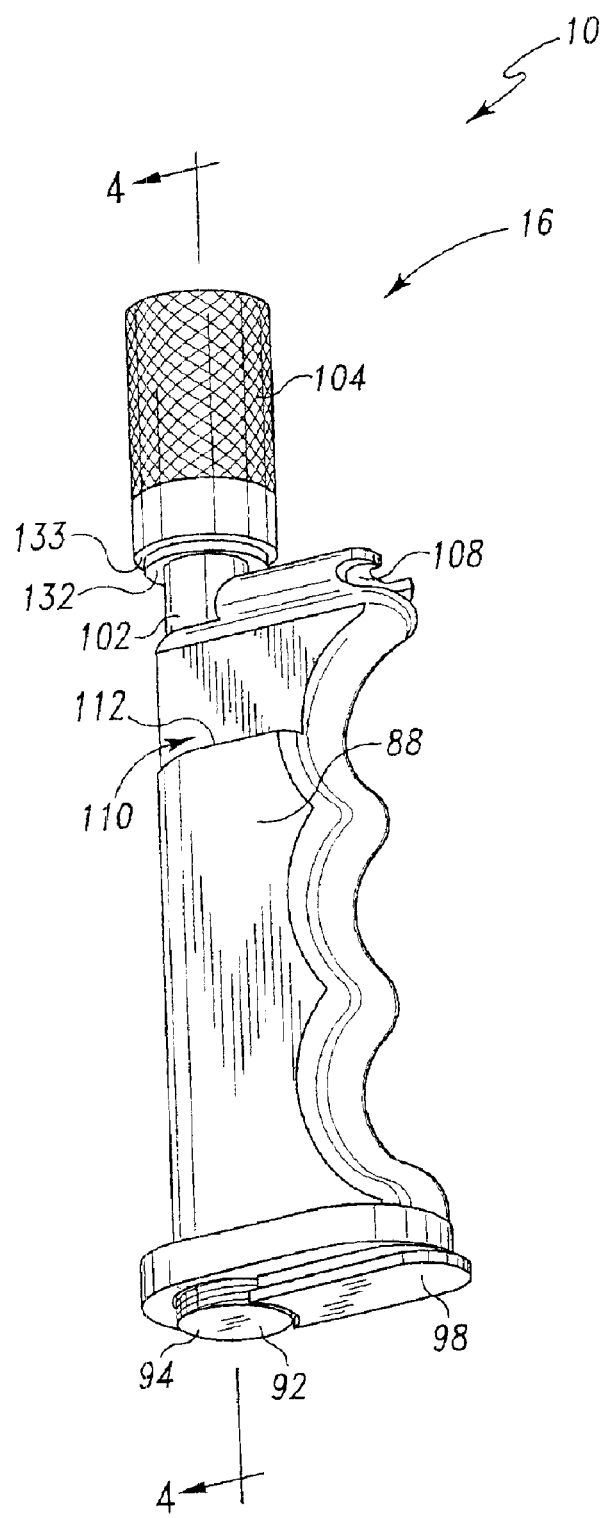
FIG. 3 is a perspective view of a bone plate locating instrument.
Figure 4:
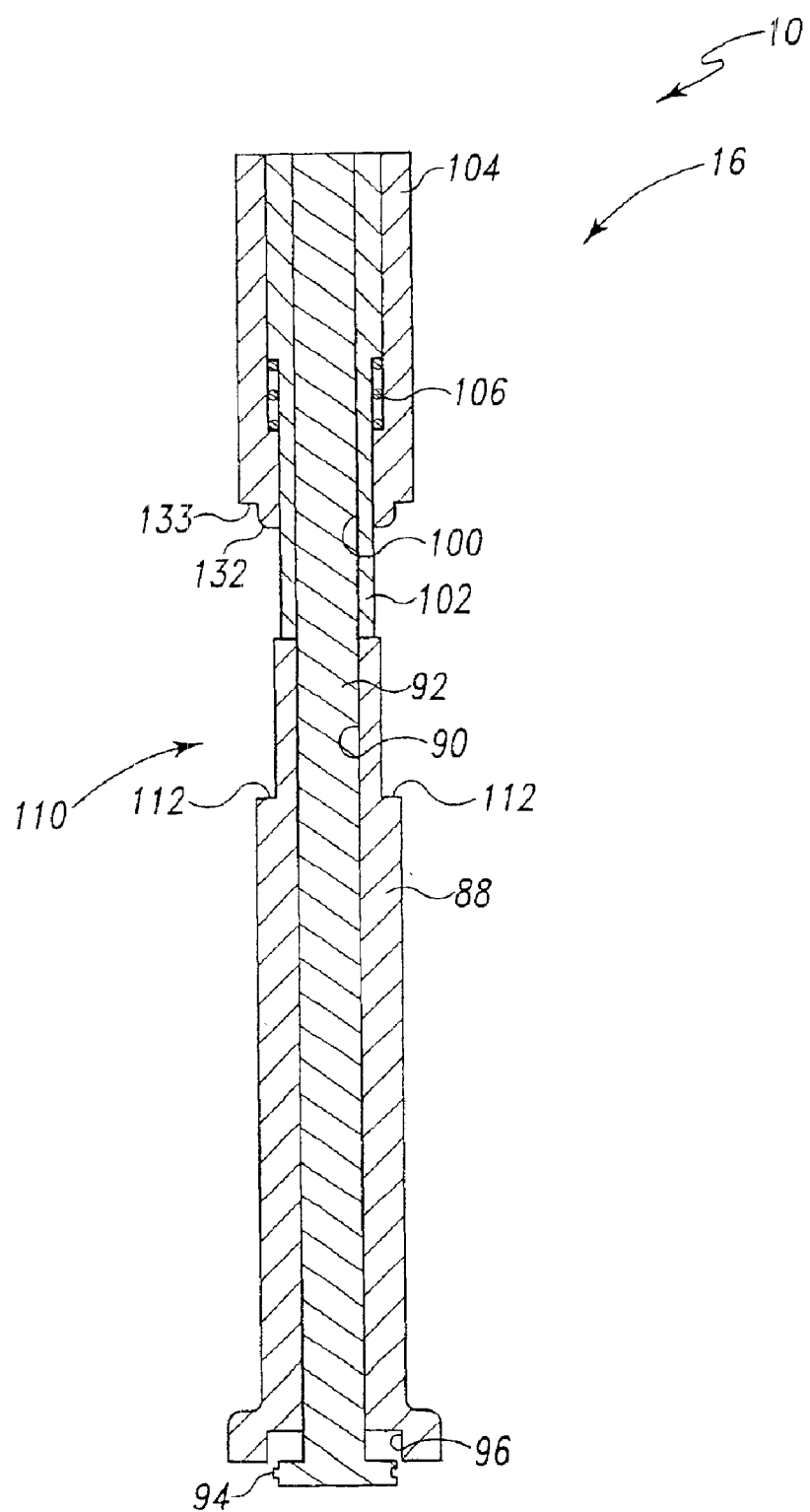
FIG. 4 is a cross sectional view taken along the line 4—4 of FIG. 3, as viewed in the direction of the arrows.

Referring now to FIGS. 3 and 4, there is shown the plate locating instrument 16 in greater detail. The plate locating instrument 16 includes a housing 88 having an elongated bore 90 extending therethrough. A rod 92 extends through the bore 90. One end of the rod 92 has a number of threads 94 defined therein and extends out of a first end of the housing 88. The housing 88 has a recess 96 defined therein. As shall be discussed below in greater detail, the threaded portion of the rod 92 is positionable in the recess 96 during securement of the plate locating instrument 16 to the bone plate 12. The housing 88 of the plate locating instrument 16 has a keying tab 98 extending from the same end thereof as the threaded portion of the rod 92. The keying tab 98 is positionable in the slot 40 of the bone plate 12 (see FIGS. 9 and 10) in order to position the bone plate 12 in a desired orientation relative to the housing 88 of the plate locating instrument 16.

As shown in FIG. 4, the end of the rod 92 opposite to the threaded portion is press fit or otherwise secured within a bore 100 defined in an inner sleeve 102. Use of the inner sleeve 102 captures the rod 92 within the housing 88 of the plate locating instrument 16. In particular, the diameter of the threads 94 is larger than the diameter of the bore 90 thereby preventing the threaded portion of the rod 92 from being retracted into the housing 88. Moreover, the outer diameter of the inner sleeve 102 is also greater than the diameter of the bore 90 thereby preventing advancement of the sleeve 102 (and hence the end of the rod 92 secured thereto) through the bore 90 in the opposite direction.

A knurled knob 104 is slidably secured to the outer surface of the inner sleeve 102. A spring 106 biases the knob 104 downwardly in the general direction of the threaded end portion 94 of the shaft 92. The spring bias exerted on the knob 104 by the spring 106 is utilized to secure the screw targeting instrument 20 to the plate locating instrument 16. In particular, the housing 88 of the plate locating instrument 16 has a channel 108 defined therein (see FIG. 3). An inverted T-shaped flange 136 defined in the screw targeting instrument 20 (see FIGS. 6 and 7) is positionable in the channel 108. As will be discussed below in greater detail, the spring 106 biases a lower surface 133 of the knob 104 into contact with an upper surface 134 of the screw targeting instrument 20 when the flange 136 of the instrument 20 is positioned in the channel 108 thereby securing the screw targeting instrument 20 to the plate positioning instrument 16.

Similar in nature to the screw locating instrument 14, the plate locating instrument 16 may be configured to include an alignment feature 110. The alignment feature 110 is provided to cooperate with features or mechanisms associated with other instruments such as the alignment feature 84 of the screw locating instrument 14 and certain features associated with the alignment instrument 18 in order to position the plate locating instrument 16 (and hence the bone plate 12) in a desired position and/or orientation.

In one exemplary embodiment, the alignment feature 110 of the plate locating instrument 16 is embodied as a pair of recesses 112. As will be discussed below in greater detail, a portion of the alignment instrument 18 may be advanced into the recesses 112 of the plate locating instrument 16, along with the recesses 84 defined in the screw locating instrument 14, in order to align or otherwise position the instruments 14, 16 in a predetermined position relative to one another.

Referring now to FIG. 5, there is shown the alignment instrument 18 in greater detail. The alignment instrument 18 is provided to position a pair of instruments, and hence the orthopaedic components secured thereto, in a desired position relative to one another. In the exemplary embodiment described herein, the alignment instrument 18 is utilized to position the screw locating instrument 14 (and hence the lag screw assembly 22 secured thereto) and the plate locating instrument 16 (and hence the bone plate 12 secured thereto) in a predetermined position relative to one another. Specifically, the alignment instrument 18 is configured to contact both the screw locating instrument 14 and the plate locating instrument 16 in a manner which causes the two instruments 14, 16 to be positioned in a predetermined position relative to one another thereby positioning the lag screw assembly 22 and the bone plate 12 in a predetermined position relative to one another.

In a more specific exemplary embodiment, the alignment instrument 18 is configured to contact both the screw locating instrument 14 and the plate locating instrument 16 in a manner which causes the two instruments 14, 16 to be moved in a predetermined manner relative to one another such that the flange 36 of the lag screw assembly 22 is advanced into the channel 44 of the bone plate 12. It should be appreciated that such movement and positioning of the screw locating instrument 14 and the plate locating instrument 16 allows for in vivo engagement of the bone plate 12 and the lag screw assembly 22 subsequent to implantation thereof.

In order to align a pair of surgical instruments in the manner described above, the alignment instrument 18 is configured to include a feature or features which cooperates with features associated with the instruments to be aligned. In the exemplary embodiment described herein, the alignment feature of the alignment instrument 18 is embodied as a pair of outwardly extending alignment members 114. In a more specific exemplary embodiment shown in FIG. 5, the alignment instrument 18 is configured as a fork-shaped instrument having a handle 116 which is secured to an arcuate-shaped body 118. In this specific exemplary embodiment, the alignment members 114 are configured as a pair of tines 120 which extend outwardly from the body 118. In such a manner, the tines 120 cooperate with the alignment features 84, 110 of the screw locating instrument 14 and the plate locating instrument 16, respectively. Specifically, the alignment instrument 18 may be advanced into contact with the screw locating instrument 14 and the plate locating instrument 16 such that the tines 120 are received into the recesses 86, 112 respectively defined therein. In such a manner, the screw locating instrument 14 and the plate locating instrument 16 are captured by the tines 120. In particular, the portion of the outer sleeve 54 of the screw locating instrument 14 located between the recesses 86, along with the portion of the body 88 of the plate locating instrument 16 located between the recesses 112, is captured or otherwise retained in a channel 122 defined between the tines 120 (see FIG. 17).

It should be appreciated that when the tines 120 of the alignment instrument 18 are positioned in the recesses 86, 112 of the instruments 14, 16, respectively, the instruments 14, 16 are positioned in a desired, predetermined position relative to one another. Specifically, the configuration of the instruments 14, 16 (e.g., the dimensional design thereof) is predetermined such that when captured by the tines 120 in the manner described above, the implantable components secured thereto (i.e., the lag screw assembly 22 and the bone plate 12) are positioned in a desired position relative to one another. As will be described below in greater detail, such alignment of the implanted components allows for in vivo assembly of an implantable orthopaedic assembly.

Referring now to FIGS. 6 and 7, there is shown the screw targeting instrument 20 in greater detail. The screw targeting instrument 20 includes a body 124 having a number of guide holes 126 defined therein. As will be discussed below in greater detail, bone screws, along with the instruments utilized for the implantation thereof, are advanced through the guide holes 126. As shown in FIG. 18, the screw targeting instrument 20 is configured such that the guide holes 126 align with the holes 42 of the bone plate 12 when the screw targeting instrument 20 and the bone plate 12 are secured to the plate locating instrument 16.

The screw targeting instrument 20 also has a slot 128 defined therein. The inner sleeve 102 (and hence the shaft 92) of the plate locating instrument 16 is received into the slot 128 during securement of the screw targeting instrument 20 to the plate locating instrument 16. Moreover, the body 124 of the screw targeting instrument 20 has a pair of cam surfaces 130 defined therein. During securement of the screw targeting instrument 20 to the plate locating instrument 16, the cam surfaces 130 urge the knob 104 upwardly. Specifically, as the inner sleeve 102 of the plate locating instrument 16 is received into the slot 128 of the screw targeting instrument 20, the cam surfaces 130 engage the lower surface 132 of the knob 104 (see FIGS. 3 and 4) thereby urging the knob 104 upwardly. Such upward movement of the knob 104 compresses the spring 106 thereby causing lower surface 132 of the knob 104 to be received into the slot 128 while also causing a shoulder surface 133 of the knob 104 to be biased downwardly onto the upper surface 134 of the body 124 of the screw targeting instrument 20. The exertion of such a spring bias on the screw targeting instrument 20 facilitates securement of the instruments 16, 20 to one another.

In operation, the surgical instrument assembly 10 may be utilized to percutaneously implant an orthopaedic assembly into the body of a patient. In the exemplary embodiment described herein, the surgical instrument assembly 10 may be utilized to implant and secure the bone plate 12 and the associated screws to the patient's femur 200. A procedure utilizing the surgical instrument assembly 10 is shown in FIGS. 12–18. Prior to performance of the surgical procedure, a number of planning steps are performed. For instance, the surgeon may review a number of anteroposterior and lateral radiographs of the patient's pelvis and affected femur 200 in order to assess, amongst other things, fracture stability, bone quality, neck-shaft angle of the femur, along with the gathering of an estimate of the length of the bone plate 12 that is to be utilized. A number of surgical templates (not shown) may be utilized to preoperatively plan such items as plate angle, plate length, and length of the lag screw (both length of the barrel and the screw itself).

Figure 12:
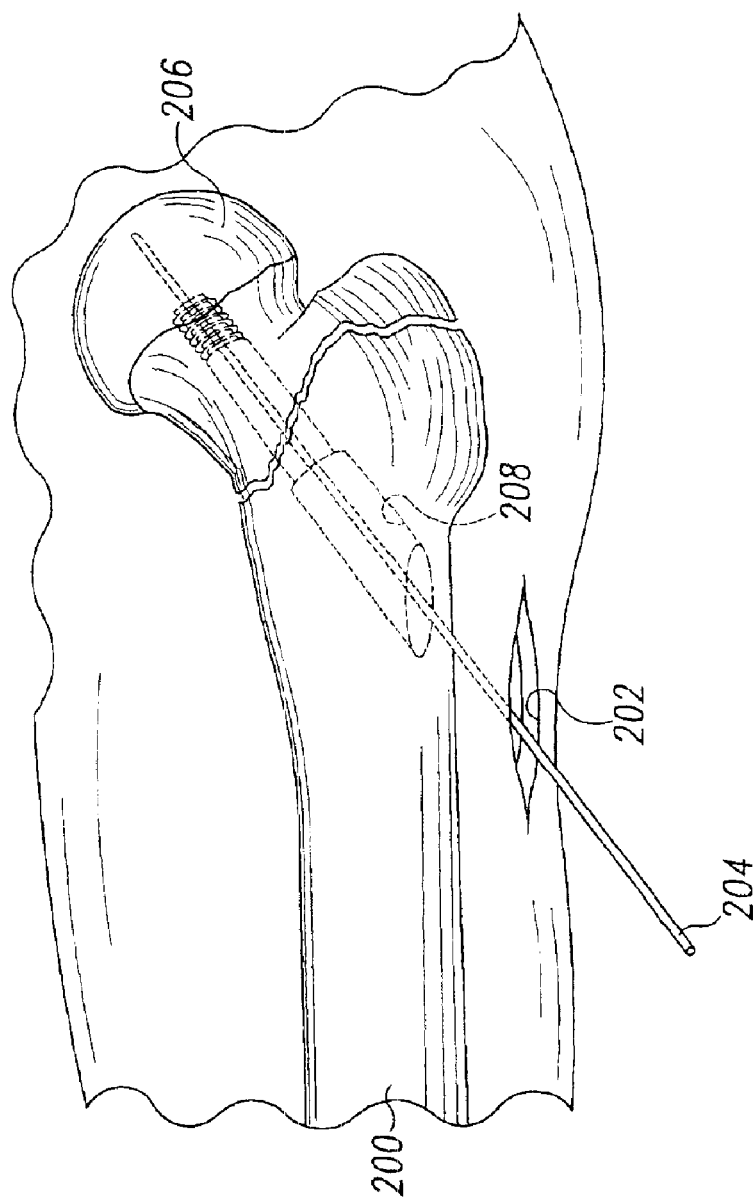
FIGS. 12–18 are diagrammatic perspective views which show a patient's femur during various steps of a procedure for percutaneously implanting the components of FIGS. 8–11.

As shown in FIG. 12, a small skin incision 202 is cut distally a total of 3–4 centimeters from the flare of the greater trochanter. The incision 202 extends through the skin along with the subcutaneous tissue thereunder to the fascia lata (not shown). The fascia lata is then incised longitudinally in line with its fibers thereby exposing the vastus lateralis muscle (not shown). Thereafter, the vastus lateralis muscle is retracted anteriorly to expose the lateral aspect of the femur 200. Once the femur 200 is exposed, a guide pin 204 is inserted into the center of the femoral head 206. Note that an image intensifier (not shown) may be used by the surgeon in order to ensure the guide pin 204 is centered in both the anterior/posterior direction and the medial/lateral direction. Thereafter, a number of cannulated reamers and taps (not shown) are utilized to form a tapped hole 208 in the femur 200 which corresponds to the lag screw assembly 22 to be utilized.

Figure 13:
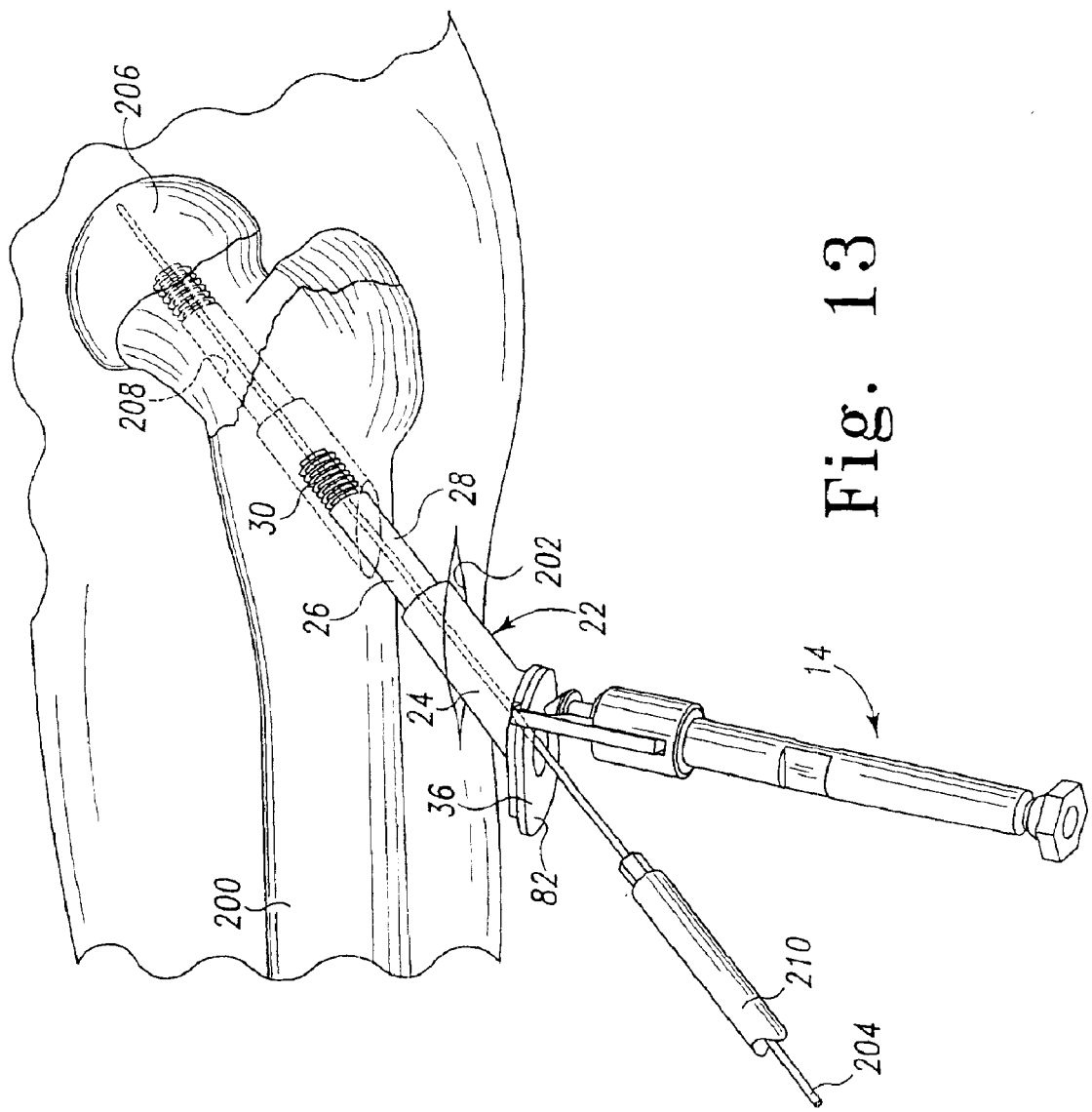

As shown in FIG. 13, once the tapped hole 208 has been formed in the femur 200, the lag screw assembly 22 is implanted and secured to the femur 200. Specifically, the screw locating instrument 14 is first secured to the lag screw assembly 22 and thereafter implanted into the body of the patient. To secure the screw locating instrument 14 to the lag screw assembly 22, the surgeon first rotates the knob 64 (and hence the rod 60) of the instrument 14 in a direction which causes the threads 68 of the rod 60 to threadingly engage the threads 70 of the sleeve 54 in a manner which retracts or otherwise urges the beveled tip 66 inwardly in a direction toward the sleeve 54. Such inward movement of the beveled tip 66 causes the cam surface 74 of the tip 66 to be urged into contact with the cam surfaces 76 of the locking arms 50 thereby overcoming the bias of the springs 58 so as to urge the locking arms 50 outwardly in a direction away from one another.

With the locking arms 50 positioned in such an extended position away from one another, the surgeon advances the instrument 14 in a manner which allows the barbs 52 of the locking arms 50 to be slipped behind the flange 36 of the lag screw assembly 22. Thereafter, the surgeon rotates the knob 64 (and hence the rod 60) of the instrument 14 in a direction which causes the threads 68 of the rod 60 to threadingly engage the threads 70 of the sleeve 54 in a manner which extends or otherwise urges the beveled tip 66 outwardly in a direction away from the sleeve 54. Such outward movement of the beveled tip 66 causes the cam surface 74 of the tip 66 to be spaced apart from the cam surface 76 of each of the locking arms 50 thereby allowing the springs 58 to urge the locking arms 50 inwardly toward one another. Such outward movement of the beveled tip 66 also causes the conically-shaped outer surface 80 thereof to be advanced into contact with the upper surface 82 of the flange 36 of the lag screw assembly 22. Such inward movement of the locking arms 50 toward one another, along with the force exerted on the upper surface 82 of the flange 36 by the beveled tip 66, causes the barbs 52 to engage or otherwise be urged into contact the backside of the flange 36 thereby securing the screw locating instrument 14 to the lag screw assembly 22, as shown in FIG. 14.

Once the screw locating instrument 14 has been secured to the lag screw assembly 22, the lag screw assembly may be implanted in the body of the patient. The guide pin 204 is used during such implantation of the lag screw assembly 22. Specifically, the shaft 28 of the screw 26 of the lag screw assembly 22 is cannulated and, as a result, is advanced along the shaft of the guide pin 204. In such a manner, the lag screw assembly 22, with the screw locating instrument 14 secured thereto, is advanced along the guide pin 204 through the incision 202 and through the underlying tissue to a location in which to the threads 30 of the screw 26 are advanced into the tapped hole 208 formed in the femur 200. A cannulated driver 210 is advanced along the guide pin 204 to assist in the implantation of the lag screw assembly 22, and may thereafter be utilized to drive the screw 26 of the lag screw assembly 22 into the femur 200 to a position in which the threads 30 of the screw 26 are centralized in the femoral head 206. Image intensification may be utilized to ensure proper location of the lag screw assembly 22. Once the lag screw assembly 22 has been fully seated in the femur 200, the guide pin 204 is removed from the femur 200.

Figure 14:
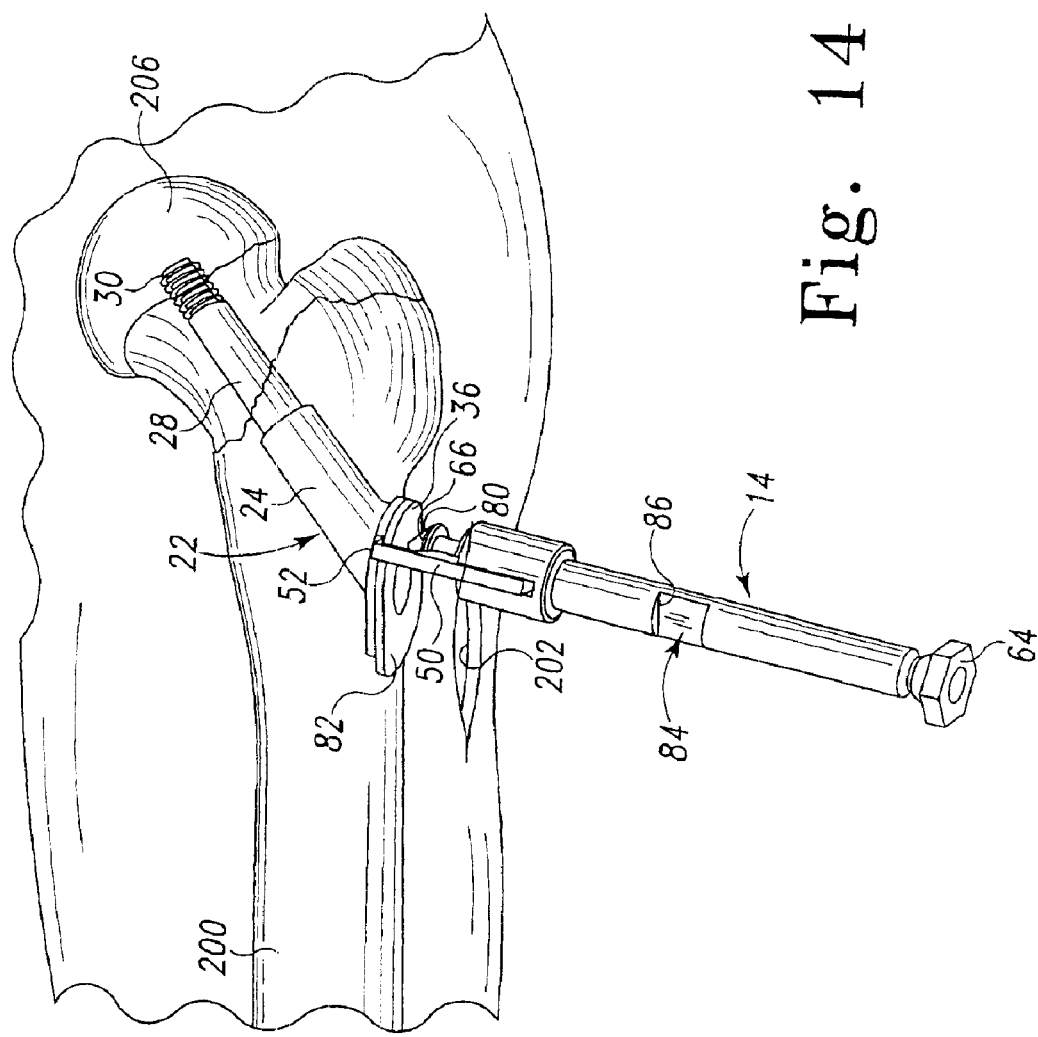
Figure 15:
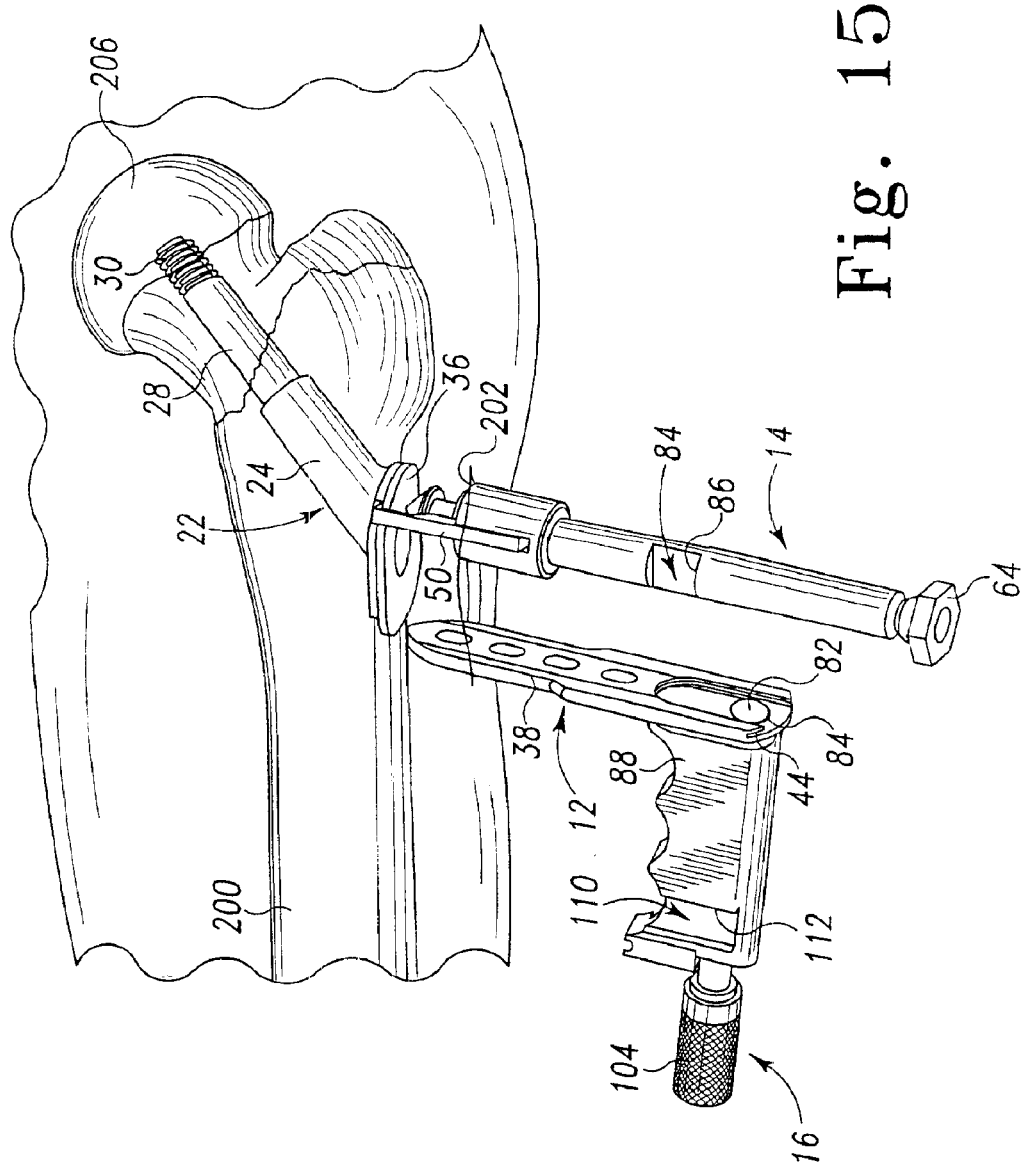

As shown in FIG. 14, when the lag screw assembly 22 is implanted in such a manner, a portion of the screw locating instrument 14 extends out of the body of the patient through the incision 202. In a specific exemplary embodiment, the alignment recesses 86 are defined in the portion of the outer sleeve 54 of the screw locating instrument 14 which extends out of the body of the patient.

The surgeon may then implant the bone plate 12 into the body of the patient. To do so, the surgeon secures the bone plate 12 that is to be implanted to the plate locating instrument 16. Specifically, the surgeon pulls upwardly on the knob 104 of the instrument 16 in order to position the threads 94 of the rod 92 into the recess 96 of the housing 88. With the threads 94 positioned in the recess 96, the surgeon advances the instrument 16 into contact with the upper surface of the bone plate 12 such that the keying tab 98 of the instrument 16 is positioned in the slot 40 of the bone plate 12. Thereafter, the surgeon rotates the knob 104 thereby causing the threads 94 of the rod 92 to threadingly engage the threads 46 defined in the bone plate 12 thereby securing the plate locating instrument 16 to the bone plate 12.

Figure 16:
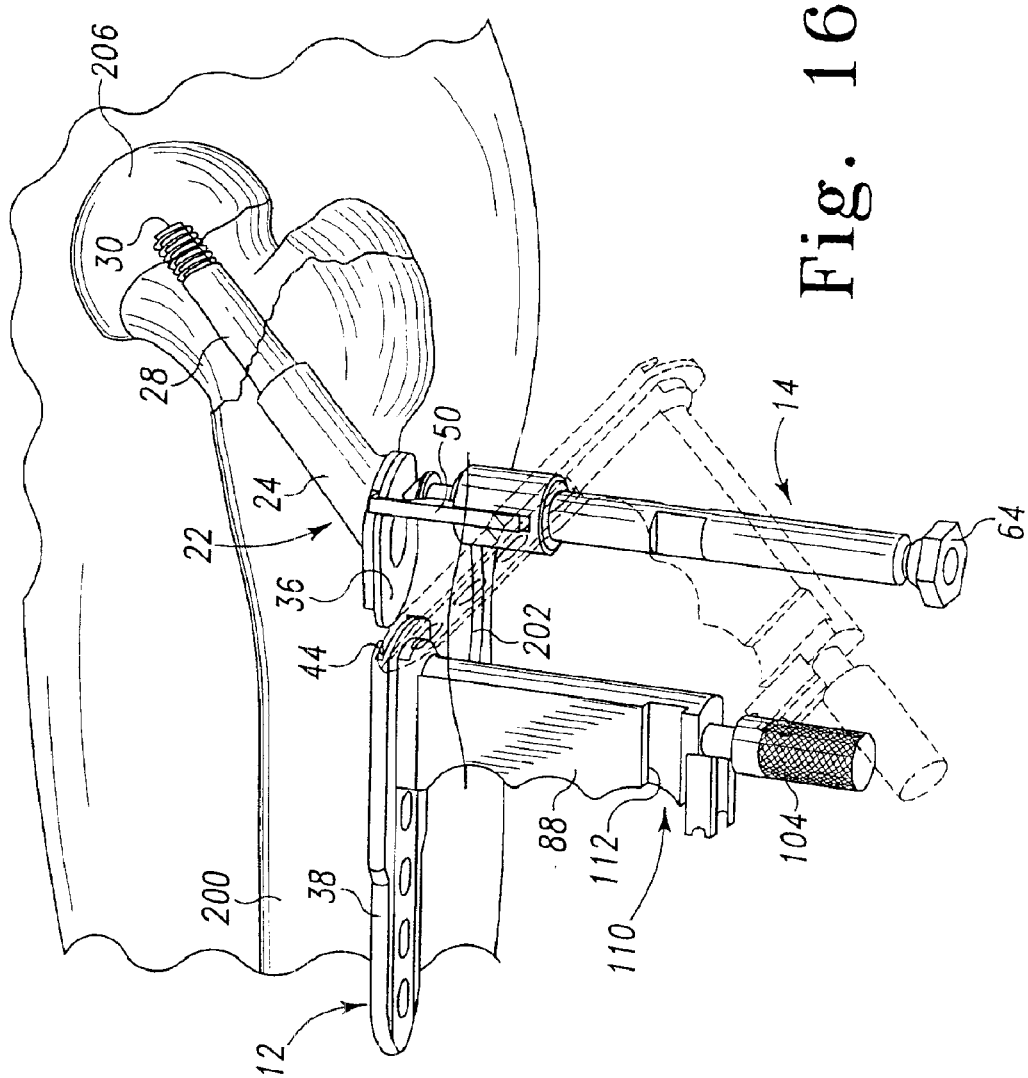

Once the instrument 16 is secured to the bone plate 12 in such a manner, the surgeon may implant the plate 12 into the body. Specifically, as shown in phantom in FIGS. 15 and 16, the surgeon advances the rounded end of the bone plate 12 is advanced through the incision 202 and the underlying tissue to a point in which the tip of the rounded end of the bone plate 12 contacts the lateral aspect of the patient's femur 200. The surgeon then manipulates the instrument 16 such the tip of the rounded end of the bone plate 12 is advanced distally along the shaft of the femur 200 (i.e., under the vastus lateralis). It should be appreciated that the shaft of the femur 200 functions as a guide for the surgeon during such distal advancement of the bone plate 12. As shown in FIG. 16, the bone plate 12 is advanced to a position in which the slotted end thereof is positioned in a location which is slightly distal to the flange 36 of the lag screw assembly 22. Moreover, as shown in FIG. 16, when the bone plate 12 is implanted in such a manner, a portion of the plate locating instrument 16 extends out of the body of the patient through the incision 202. In a specific exemplary embodiment, the alignment recesses 112 are defined in the portion of the housing 88 of the plate locating instrument 16 which extends out of the body of the patient.

Once the bone plate 12 has been implanted in such a manner, the surgeon may secure the bone plate 12 and the lag screw assembly 22 to one another. In order to do so, the surgeon may utilize the alignment instrument 18. Specifically, the alignment instrument 18 may be advanced into contact with both instruments 14, 16 in order to position the instruments 14, 16 (and hence the components secured thereto) in a predetermined position relative to one another.

In the specific exemplary embodiment described herein, the surgeon grasps the handle 116 of the fork-shaped alignment instrument 18 and advances the tines 120 thereof into cooperation with the alignment features 84, 110 of the screw locating instrument 14 and the plate locating instrument 16, respectively. Specifically, the alignment instrument 18 is advanced by the surgeon into contact with the screw locating instrument 14 and the plate locating instrument 16 such that the tines 120 are received into the recesses 86, 112, respectively. In such a manner, the portion of the outer sleeve 54 of the screw locating instrument 14 located between the recesses 86, along with the portion of the body 88 of the plate locating instrument 16 located between the recesses 112, is captured or otherwise retained in the channel 122 defined between the tines 120 (see FIG. 17).

As described above, when the tines 120 of the alignment instrument 18 are positioned in the recesses 86, 112 of the instruments 14, 16, respectively, the instruments 14, 16 are positioned in a desired, predetermined position relative to one another. Specifically, the configuration of the instruments 14, 16 (e.g., the dimensional design thereof) is predetermined such that when captured by the tines 120 in the manner described above, the implantable components secured thereto (i.e., the lag screw assembly 22 and the bone plate 12) are positioned in a desired position relative to one another.

In the specific exemplary embodiment described herein, capturing the instruments 14, 16 with the tines 120 causes the channel 44 of the bone plate 12 to be aligned with the distal edge of the flange 36 of the lag screw assembly 22. As the two instruments 14, 16 are advanced toward one another within the tines 120 of the alignment instrument 18, the distal edge of the flange 36 is received into the channel 44 of the bone plate 12.

Once a portion of the distal edge of the flange 36 has been received into the channel 44 of the bone plate 12, the alignment instrument 18 is removed from the instruments 14, 16. Specifically, the alignment instrument 18 is moved by the surgeon in a manner which causes the tines 120 to be removed from the recesses 86, 112 of the instruments 14, 16, respectively.

Thereafter, the screw locating instrument 14 may be detached from the lag screw assembly 22. Specifically, the surgeon rotates the knob 64 (and hence the rod 60) of the instrument 14 in a direction which causes the threads 68 of the rod 60 to threadingly engage the threads 70 of the sleeve 54 in a manner which retracts or otherwise urges the beveled tip 66 inwardly in a direction toward the sleeve 54. Such inward movement of the beveled tip 66 causes the cam surface 74 of the tip 66 to be urged into contact with the cam surfaces 76 of the locking arms 50 thereby overcoming the bias of the springs 58 so as to urge the locking arms 50 outwardly in a direction away from one another. Once the locking arms 50 have been moved away from each other in such a manner, the surgeon manipulates the screw locating instrument 14 in a manner which slips the barbs 52 back around from the backside of the flange 36 of the lag screw assembly 22 thereby releasing the instrument 14 from the lag screw assembly 22. Once detached from the lag screw assembly 22, the surgeon advances the screw locating instrument 14 out of the body of the patient through the incision 202.

Thereafter, the surgeon urges or otherwise moves the plate locating instrument 16 proximally in order to further advance the flange 36 of the lag screw assembly 22 into the channel 44 of the bone plate 12. As shown in FIG. 18, the surgeon continues to advance the plate locating instrument 16 (and hence the plate 12 secured thereto) in a proximal direction until the flange 36 is fully seated in the channel 44.

Thereafter, the surgeon may begin to insert bone screws 212 into each of the holes 42 of the bone plate 12. In order to do so, as shown in FIG. 18, the screw targeting instrument 20 is secured to the plate locating instrument 16. In particular, the surgeon advances the screw targeting instrument 20 into contact with the plate locating instrument 16 in a manner which causes the inner sleeve 102 of the plate locating instrument 16 to be received into the slot 128 of the screw targeting instrument 20. During such advancement of the screw targeting instrument 20 into contact with the plate locating instrument 16, the cam surfaces 130 of the screw targeting instrument 20 urge the knob 104 upwardly. Specifically, as the inner sleeve 102 of the plate locating instrument 16 is received into the slot 128 of the screw targeting instrument 20, the cam surfaces 130 engage the lower surface 132 of the knob 104 (see also FIGS. 3 and 4) thereby urging the knob 104 upwardly. Such upward movement of the knob 104 compresses the spring 106 thereby causing the lower surface 132 of the knob 104 to be advanced into the slot 128, while causing the shoulder surface 133 of the knob 104 to be biased downwardly onto the upper surface 134 of the body 124 of the screw targeting instrument 20. The exertion of such a spring bias on the screw targeting instrument 20 facilitates securement of the instruments 16, 20 to one another.

As described above, the screw targeting instrument 20 is configured such that the guide holes 126 align with the holes 42 of the bone plate 12 when the screw targeting instrument 20 and the bone plate 12 are secured to the plate locating instrument 16. Hence, as shown in FIG. 18, once the screw targeting instrument 20 has been secured to the plate locating instrument 16, the bone screws 212 are percutaneously secured to the bone plate 12. Specifically, the shaft 216 of a screw driving instrument 214 is advanced through one of the guide holes 126 defined in the screw targeting instrument 20. A number of percutaneous, self-tapping bone screws 212 are then advanced by the driving instrument 214 through the skin and the underlying tissue via a stab incision 220 and into one of the holes 42 of the bone plate 12. Each of the screws 212 is driven into the femur 200 until the head 218 engages the bone plate 12. It should be appreciated that one of the screws 212 is advanced into each of the remaining holes 42 of the bone plate 12.

Once each of the screws 212 is installed, the screw targeting device 20 is detached from the plate locating instrument 16. Thereafter, the surgeon rotates the knob 104 of the plate locating instrument 16 in a direction which causes the threads 94 of the rod 92 to threadingly disengage the threads 46 defined in the bone plate 12. Once the threads 94 of the rod 92 have disengaged the threads 46 of the bone plate 12, the surgeon manipulates the plate locating instrument 16 such that the keying tab 98 of the instrument 16 is removed from the slot 40 of the bone plate 12 thereby detaching the plate locating instrument 16 from the bone plate 12. The surgeon then advances the plate locating instrument 16 out of the body of the patient through the incision 202.

Once the plate locating instrument 16 has been removed from the patient's body, the surgeon completes the surgical procedure. Specifically, the surgeon utilizes routine closure techniques to close the incision 202 along with the stab incisions 220 created during the installation of each of the bone screws 212.

As shown in FIGS. 19–23, a bone screw insertion assembly 222 may be used during the installation of the bone screws 212. The assembly 222 includes a screw sleeve 224 (see FIGS. 19 and 20), a drill guide 226 (see FIG. 21), a trocar 228 (see FIG. 22), and a bone drill 230 (see FIG. 23). The screw sleeve 224 includes a cannula 232 having a central passage 234 defined therein. The screw sleeve 224 also includes a hollow knob 236 having a number of threads 238 defined therein.

The drill guide 226 includes a cannula 242 having a central passage 244 defined therein. The drill guide 226 also includes a hollow knob 246 having a number of threads 248 defined therein. The drill guide 226 is securable to the screw sleeve 224. Specifically, the outer surface of the cannula 242 of the drill guide 226 has a number of threads 250 defined therein which threadingly engage the threads 238 of the screw sleeve when the cannula 242 of the drill guide 226 is inserted into the central passage 234 of the cannula 232 of the screw sleeve 224.

The trocar 228 has an elongated obturator 252 having a distal tip 254 for puncturing tissue, and a knob 256. The trocar 228 is securable to the drill guide 226. In particular, the outer surface of the upper portion of the obturator 252 of the trocar 228 has a number of threads 258 defined therein which threadingly engage the threads 248 of the drill guide 226 when the obturator 252 of the trocar 228 is inserted into the central passage 244 of the cannula 242 of the drill guide 226.

The assembly 222 may be used by the surgeon to facilitate proper insertion of the bone screws 212. To do so, the trocar 228 is first secured within the cannula 242 of the drill guide 226, which is in turn secured within the cannula 232 of the screw sleeve 224. Thereafter, the assembled instruments (i.e., the screw sleeve 224, the drill guide 226, and the trocar 228) are advanced through one of the guide holes 126 of the screw targeting instrument 20 (see FIGS. 6, 7, and 18). Thereafter, the trocar 228 is utilized to penetrate through one of the stab incisions 220. Specifically, when assembled in such a manner, the tip 254 of the obturator 252 extends out of both the cannula 242 of the drill guide 226 and the cannula 232 of the screw sleeve 224 thereby allowing the tip 254 to be utilized to puncture the underlying tissue.

During advancement of the assembled instruments through the underlying tissue, the screw sleeve 224 may be used to engage the bone plate 12 in order to align the assembled instruments with the holes 42 of the bone plate 12. Specifically, the distal end of the cannula 232 of the screw sleeve 224 has an alignment mechanism or feature in the form of a pair of downwardly extending flanges 260 defined therein. The flanges 260 are received into the oval-shaped holes 42 of the bone plate 212. During such advancement of the flanges 260 into the holes 42, the flanges 260 contact the sidewalls surrounding the holes 42 thereby causing the cannulae 232, 242, and hence the tip 254 of the trocar 228, to be "centered" or otherwise aligned within the holes 42 of the bone plate 12.

Once the flanges 260 of the screw sleeve 224 are positioned in the holes 42 of the bone plate 12, the trocar 228 may be unscrewed from the drill guide 226 and removed therefrom. Thereafter, a drilling tip 262 of the bone drill 230 is advanced through the cental passage 244 of the drill guide 226 and operated to drill a hole in the femur 200. It should be appreciated that the diameter of the bone drill 230 is approximately equal to the minor diameter of the bone screws 212. Once the bone drill 230 has been used by the surgeon to drill a hole to the desired depth in the femur 200, the drill 230 is removed from the drill guide 226. Thereafter, the drill guide 226 is unscrewed from the screw sleeve 224 and removed therefrom.

The screw driving instrument 214 (see FIG. 18), with a bone screw 212 positioned on the end thereof, is then advanced through the screw sleeve 224. The screw driving instrument 214 is then operated to drive the screw 212 into the femur 200 until the head 218 of the screw 212 engages the bone plate 12. It should be appreciated that during such a screw insertion procedure, the screw sleeve 224 functions as a tissue protector for protecting the soft tissue in the surrounding areas.

The screw sleeve 224 may then be removed from the body of the patient. Thereafter, the remaining bone screws 212 may be inserted in a similar manner. Once done, the stab incisions 220 may be closed in the manner described above.

While the invention has been illustrated and described in detail in the drawings and foregoing description, such an illustration and description is to be considered as exemplary and not restrictive in character, it being understood that only the illustrative embodiments have been shown and described and that all changes and modifications that come within the spirit of the invention are desired to be protected.

There are a plurality of advantages of the present invention arising from the various features of the orthopaedic components, instruments, and associated surgical techniques described herein. It will be noted that alternative embodiments of each of the orthopaedic components, instruments, and associated surgical techniques of the present invention may not include all of the features described yet still benefit from at least some of the advantages of such features. Those of ordinary skill in the art may readily devise their own implementations of orthopaedic components, instruments, and associated surgical techniques that incorporate one or more of the features of the present invention and fall within the spirit and scope of the present invention as defined by the appended claims.

For example, it should be appreciated that although the screw locating instrument 14 is herein described as being secured to the lag screw assembly 22 prior to implantation of the lag screw assembly 22, other configurations and techniques are also contemplated for use in regard to the present invention. For example, the screw locating instrument may be secured to the lag screw in vivo subsequent to implantation of the lag screw assembly 22. Similarly, it should be appreciated that plate locating instrument 16 may also be secured to the bone plate 12 in vivo subsequent to implantation of the bone plate 12.

What is claimed is:

1. An instrument assembly, comprising:

a screw locating instrument which is adapted to be secured to a hip screw, said screw locating instrument having a first recess defined therein;

a plate locating instrument which is adapted to be secured to a bone plate, said plate locating instrument having a second recess defined therein; and an alignment instrument having an alignment member extending therefrom, wherein both said first recess and said second recess are adapted to receive said alignment member therein.

2. The instrument assembly of claim 1, said plate locating instrument is further adapted to be secured to said bone plate prior to implantation of said bone plate into a body of a patient.

3. The instrument assembly of claim 1, wherein said screw locating instrument is further adapted to be secured to said hip screw prior to implantation of said hip screw into a body of a patient.

4. An orthopaedic implant and instrument assembly, comprising:

a bone screw which is adapted to be screwed into a bone, a bone plate which is adapted to be secured to said bane screw, a first instrument which is adapted to be secured to said bone screw, said first instrument having a first recess defined therein;

a second instrument which is adapted to be secured to said bone plate, said second instrument having a second recess defined therein; and a third instrument having an alignment member extending therefrom, wherein both said first recess and said second recess are adapted to receive said alignment member therein.

5. The instrument assembly of claim 4, wherein said first instrument is further adapted to be secured to said bone screw prior to implantation of said bone screw into a body of a patient.

6. The instrument assembly of claim 4, wherein said first instrument is to secured to said bone screw subsequent to implantation of said bone screw into a body of a patient.

7. The instrument assembly of claim 4, wherein:

said bone screw has a flange secured thereto, said bone plate has a channel defined therein, and said flange is aligned with said channel when (i) said bone screw is secured to said first instrument, (ii) said bone plate is secured to said second instrument, and (iii) said alignment member is received into both said first recess and said second recess.

\* \* \* \* \*